(12) United States Patent
Roeben et al.

(10) Patent No.: US 10,562,923 B2
(45) Date of Patent: Feb. 18, 2020

(54) SILANE MIXTURES AND PROCESSES FOR PREPARATION THEREOF

(71) Applicant: Evonik Degussa GmbH, Essen (DE)

(72) Inventors: Caren Roeben, Essen (DE); Ralph Moser, Jersey City, NJ (US); Alexander Koepfer, Bernau im Schwarzwald (DE); Stefanie Mayer, Rheinfelden (DE); Andre Hasse, Juelich (DE); Frank Forster, Schoellkrippen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/201,568

(22) Filed: Nov. 27, 2018

(65) Prior Publication Data

US 2019/0161506 A1 May 30, 2019

(30) Foreign Application Priority Data

Nov. 28, 2017 (DE) .................. 10 2017 221 259

(51) Int. Cl.
C07F 7/18 (2006.01)
(52) U.S. Cl.
CPC .................. C07F 7/1892 (2013.01)
(58) Field of Classification Search
None
See application file for complete search history.

(56) References Cited

U.S. PATENT DOCUMENTS

| 7,423,165 B2 | 9/2008 | Korth et al. |
| 7,767,742 B2 | 8/2010 | Krafczyk et al. |
| 8,013,178 B2 | 9/2011 | Klockmann et al. |
| 8,236,882 B2 | 8/2012 | Klockmann et al. |
| 9,617,287 B2 | 4/2017 | Klockmann et al. |

FOREIGN PATENT DOCUMENTS

WO WO-2006013060 A1 * 2/2006 ............. C08G 77/28

OTHER PUBLICATIONS

Search Report dated Apr. 25, 2019 in the corresponding European Application No. 18206633.2 (with English Translation of Category of Cited Documents) 8 pages.
Wilson, J.R. H., et al., "Substituted organopolysiloxanes and use thereof", XP55580411, Jan. 1, 2006, pp. 1-3.
Vlasova, N. N., et al., "Photochemical addition of 1,2-ethanediol to alkenyltrichloro- and triorganylalkenylsilanes", Journal of General Chemistry U, Consultants Bureau, Bd. 53. Nr. 2., XP009086174, Jan. 1, 1983, pp. 329-333.
U.S. Appl. No. 10/443,167, filed May 22, 2003, 2003-0229166 A1, Roland Krafczyk, et al.
U.S. Appl. No. 10/254,658, filed Jul. 10, 2003, 2003-0130388 A1, Hans-Detlef Luginsland, et al.
U.S. Appl. No. 15/781,223, filed Jul. 28, 2016, Caren Roeben, et al.

* cited by examiner

Primary Examiner — Clinton A Brooks
Assistant Examiner — Kofi Adzamli
(74) Attorney, Agent, or Firm — Oblon, McClelland, Maier & Neustadt, L.L.P.

(57) ABSTRACT

The invention relates to silane mixtures comprising a silane of the formula I $(R^1)_y(R^2)_{3-y}Si-R^3-(S-R^4)_n-S-R^5$ (I)

and a silane of the formula II $(R^1)_y(R^2)_{3-y}Si-R^3-(S-R^4)_z-S-R^3-Si(R^1)_y(R^2)_{3-y}$ (II)

where the molar ratio of silane of the formula I to silane of the formula II is 20:80-90:10.
The silane mixture according to the invention can be prepared by mixing the silanes of the formula I and silanes of the formula II.

12 Claims, No Drawings

SILANE MIXTURES AND PROCESSES FOR PREPARATION THEREOF

The invention relates to silane mixtures and to processes for preparation thereof.

EP 0670347 and EP 0753549 disclose rubber mixtures comprising at least one crosslinker, a filler, optionally further rubber auxiliaries and at least one reinforcing additive of the formula $$R^1R^2R^3Si-X^1-(-S_x-Y-)_m-(-S_x-X^2-SiR^1R^2R^3)_n.$$

JP2012149189 discloses the silane of the formula $(R^1O)_l R^2_{(3-l)}Si-R^3-(S_mR^4)_n-S-R^5$ with $R^5=-C(=O)-R^6$ $R^6=C1-C20$.

In addition, EP 1375504 discloses silanes of the formula $$(R^1O)_{(3-P)}(R^2)_PSi-R^3-S_m-R^4-(S_n-R^4)_q-S_m-R^3-Si(R^2)_P(OR^1)_{(3-P)}.$$

WO 2005059022 discloses rubber mixtures comprising a silane of the formula $$[R^2R^3R^4Si-R^5-S-R^6-R^7-]R^1.$$

Additionally known are rubber mixtures comprising a bifunctional silane and a further silane of the formula (Y)G(Z) (WO 2012/092062) and rubber mixtures comprising bistriethloxysilylpropyl polysulfide and bistriethoxysilylpropyl monosulfide (EP1085045).

EP 1928949 discloses a rubber mixture comprising the silanes $(H_5C_2O)_3Si-(CH_2)_3-X-(CH_2)_6-S_2-(CH_2)_6-X-(CH_2)_3-Si(OC_2H_5)_3$ and/or $(H_5C_2O)_3Si-(CH_2)_3-X-(CH_2)_{10}-S_2-(CH_2)_6-X-(CH_2)_{10}-Si(OC_2H_5)_3$ and $(H_5C_2O)_3Si-(CH_2)_3-S_m-(CH_2)_3-Si(OC_2H_5)_3$.

It is an object of the present invention to provide silane mixtures which lead to rubber mixtures having improved rolling resistance compared to silanes known from the prior art. Moreover, the silane mixtures according to the invention lead to an advantageous resolution in the trade-off between rolling resistance and wet grip.

The invention provides a silane mixture comprising a silane of the formula I $$(R^1)_y(R^2)_{3-y}Si-R^3-(S-R^4)_n-S-R^5 \quad (I)$$

and a silane of the formula II $$(R^1)_y(R^2)_{3-y}Si-R^3-(S-R^4)_z-S-R^3-Si(R^1)_y(R^2)_{3-y} \quad (II)$$

where $R^1$ are the same or different and are C1-C10-alkoxy groups, preferably methoxy or ethoxy groups, phenoxy group, C4-C10-cycloalkoxy groups or alkyl polyether group $-O-(R^6-O)_r-R^7$ where $R^6$ are the same or different and are a branched or unbranched, saturated or unsaturated, aliphatic, aromatic or mixed aliphatic/aromatic divalent C1-C30 hydrocarbon group, preferably $-CH_2-CH_2-$, r is an integer from 1 to 30, preferably 3 to 10, and $R^7$ is unsubstituted or substituted, branched or unbranched monovalent alkyl, alkenyl, aryl or aralkyl groups, preferably a $C_{13}H_{27}$-alkyl group, $R^2$ are the same or different and are C6-C20-aryl groups, preferably phenyl, C1-C10-alkyl groups, preferably methyl or ethyl, C2-C20-alkenyl group, C7-C20-aralkyl group or halogen, preferably Cl, $R^3$ are the same or different and are a branched or unbranched, saturated or unsaturated, aliphatic, aromatic or mixed aliphaticiaromatic divalent C1-C30 hydrocarbon group, preferably C1-C20, more preferably C1-C10, even more preferably C2-C7, especially preferably $CH_2CH_2$ and $CH_2CH_2CH_2$, $R^4$ are the same or different and are a branched or unbranched, saturated or unsaturated, aliphatic, aromatic or mixed aliphatic/aromatic divalent C1-C30 hydrocarbon group, preferably C1-C20, more preferably C1-C10, even more preferably C2-C7, especially preferably $(CH_2)_6$, $R^5$ is hydrogen or a $-C(=O)-R^8$ group with $R^8$=hydrogen, a C1-C20 alkyl group, preferably C1-C17, C6-C20-aryl groups, preferably phenyl, C2-C20-alkenyl group, C7-C20-aralkyl group, and n is 1, 2 or 3, preferably 1 or 2, more preferably 1, y are the same or different and are 1, 2 or 3, z is 1, 2 or 3, preferably 1, and the molar ratio of silane of the formula I to silane of the formula II is 20:80-90:10, preferably 25:75-85:15, more preferably 25:75-80:20, most preferably 30:70-75:25.

Preferably, the silane mixture may comprise a silane of the formula I $$(R^1)_y(R^2)_{3-y}Si-R^3-(S-R^4)_n-S-R^5 \quad (I)$$

and a silane of the formula II $$(R^1)_y(R^2)_{3-y}Si-R^3-(S-R^4)_z-S-R^3-Si(R^1)_y(R^2)_{3-y} \quad (II)$$

where n is 1, z is 1 and $R^1$, $R^2$, $R^3$, $R^4$, $R^5$ and y have the same definition as described above.

The silane mixture according to the invention may comprise further additives or consist solely of silanes of the formula I and silanes of the formula II.

The silane mixture according to the invention may comprise oligomers that form as a result of hydrolysis and condensation of the silanes of the formula I and/or silanes of the formula II.

The silane mixture according to the invention may have been applied to a support, for example wax, polymer or carbon black. The silane mixture according to the invention may have been applied to a silica, in which case the binding may be physical or chemical.

$R^3$ and $R^4$ may independently be $-CH_2-$, $-CH_2CH_2-$, $-CH_2CH_2CH_2-$, $-CH_2CH_2CH_2CH_2-$, $-CH(CH_3)-$, $-CH_2CH(CH_3)-$, $-CH(CH_3)CH_2-$, $-C(CH_3)_2-$, $-CH(C_2H_5)-$, $-CH_2CH_2CH(CH_3)-$, $-CH(CH_3)CH_2CH_2-$, $-CH_2CH(CH_3)CH_2-$, $-CH_2CH_2CH_2CH_2CH_2-$, $-CH_2CH_2CH_2CH_2CH_2CH_2-$, $-CH_2CH_2CH_2CH_2CH_2CH_2CH_2-$, $-CH_2CH_2CH_2CH_2CH_2CH_2CH_2CH_2-$, $-CH_2CH_2CH_2CH_2CH_2CH_2CH_2CH_2CH_2-$, $-CH_2CH_2CH_2CH_2CH_2CH_2CH_2CH_2CH_2CH_2-$, $-CH_2CH_2CH_2CH_2CH_2CH_2CH_2CH_2CH_2CH_2CH_2-$, $-CH_2CH_2CH_2CH_2CH_2CH_2CH_2CH_2CH_2CH_2CH_2CH_2-$, $-CH_2CH_2CH_2CH_2CH_2CH_2CH_2CH_2CH_2CH_2CH_2CH_2CH_2-$, $-CH_2CH_2CH_2CH_2CH_2CH_2CH_2CH_2CH_2CH_2CH_2CH_2CH_2CH_2-$, $-CH_2CH_2CH_2CH_2CH_2CH_2CH_2CH_2CH_2CH_2CH_2CH_2CH_2CH_2CH_2-$ or $R^1$ may preferably be methoxy or ethoxy.
$R^5$ may preferably be $-C(=O)-CH_3$, $-C(=O)-C_2H_5$, $-C(=O)-C_3H_7$, $-C(=O)-C_4H_9$, $-C(=O)-$ $C_5H_{11}$, —C(=O)—$C_6H_{13}$, —C(=O)—$C_7H_{15}$, —C(=O)—$C_8H_{17}$, —C(=O)—$C_9H_{19}$, —C(=O)—$C_{10}H_{21}$, —C(=O)—$C_{11}H_{23}$, —C(=O)—$C_{12}H_{25}$, —C(=O)—$C_{13}H_{27}$, —C(=O)—$C_{14}H_{29}$, —C(=O)—$C_{15}H_{31}$, —C(=O)—$C_{16}H_{33}$ or —C(=O)—$C_{17}H_{35}$.

Silanes of the formula I may preferably be:
(EtO)$_3$Si—(CH$_2$)$_3$—S—(CH$_2$)—S—C(=O)—CH$_3$,
(EtO)$_3$Si—(CH$_2$)$_3$—S—(CH$_2$)—S—C(=O)—C$_2$H$_5$,
(EtO)$_3$Si—(CH$_2$)$_3$—S—(CH$_2$)—S—C(=O)—C$_3$H$_7$,
(EtO)$_3$Si—(CH$_2$)$_3$—S—(CH$_2$)—S—C(=O)—C$_4$H$_9$,
(EtO)$_3$Si—(CH$_2$)$_3$—S—(CH$_2$)—S—C(=O)—C$_5$H$_{11}$,
(EtO)$_3$Si—(CH$_2$)$_3$—S—(CH$_2$)—S—C(=O)—C$_6$H$_{13}$,
(EtO)$_3$Si—(CH$_2$)$_3$—S—(CH$_2$)—S—C(=O)—C$_7$H$_{15}$,
(EtO)$_3$Si—(CH$_2$)$_3$—S—(CH$_2$)—S—C(=O)—C$_9$H$_{19}$,
(EtO)$_3$Si—(CH$_2$)$_3$—S—(CH$_2$)—S—C(=O)—C$_{11}$H$_{23}$,
(EtO)$_3$Si—(CH$_2$)$_3$—S—(CH$_2$)—S—C(=O)—C$_{13}$H$_{27}$,
(EtO)$_3$Si—(CH$_2$)$_3$—S—(CH$_2$)—S—C(=O)—C$_{15}$H$_{31}$,
(EtO)$_3$Si—(CH$_2$)$_3$—S—(CH$_2$)—S—C(=O)—C$_{17}$H$_{35}$,
(EtO)$_3$Si—(CH$_2$)$_3$—S—(CH$_2$)$_2$—S—C(=O)—CH$_3$,
(EtO)$_3$Si—(CH$_2$)$_3$—S—(CH$_2$)$_2$—S—C(=O)—C$_2$H$_5$,
(EtO)$_3$Si—(CH$_2$)$_3$—S—(CH$_2$)$_2$—S—C(=O)—C$_3$H$_7$,
(EtO)$_3$Si—(CH$_2$)$_3$—S—(CH$_2$)$_2$—S—C(=O)—C$_4$H$_9$,
(EtO)$_3$Si—(CH$_2$)$_3$—S—(CH$_2$)$_2$—S—C(=O)—C$_5$H$_{11}$.
(EtO)$_3$Si—(CH$_2$)$_3$—S—(CH$_2$)$_2$—S—C(=O)—C$_6$H$_{13}$,
(EtO)$_3$Si—(CH$_2$)$_3$—S—(CH$_2$)$_2$—S—C(=O)—C$_7$H$_{15}$
(EtO)$_3$Si—(CH$_2$)$_3$—S—(CH$_2$)$_2$—S—C(=O)—C$_9$H$_{19}$,
(EtO)$_3$Si—(CH$_2$)$_3$—S—(CH$_2$)$_2$—S—C(=O)—C$_{11}$H$_{23}$,
(EtO)$_3$Si—(CH$_2$)$_3$—S—(CH$_2$)$_2$—S—C(=O)—C$_{13}$H$_{27}$,
(EtO)$_3$Si—(CH$_2$)$_3$—S—(CH$_2$)$_2$—S—C(=O)—C$_{15}$H$_{31}$,
(EtO)$_3$Si—(CH$_2$)$_3$—S—(CH$_2$)$_2$—S—C(=O)—C$_{17}$H$_{35}$,
(EtO)$_3$Si—(CH$_2$)$_3$—S—(CH$_2$)$_3$—S—C(=O)—CH$_3$,
(EtO)$_3$Si—(CH$_2$)$_3$—S—(CH$_2$)$_3$—S—C(=O)—C$_2$H$_5$,
(EtO)$_3$Si—(CH$_2$)$_3$—S—(CH$_2$)$_3$—S—C(=O)—C$_3$H$_7$,
(EtO)$_3$Si—(CH$_2$)$_3$—S—(CH$_2$)$_3$—S—C(=O)—C$_4$H$_9$,
(EtO)$_3$Si—(CH$_2$)$_3$—S—(CH$_2$)$_3$—S—C(=O)—C$_5$H$_{11}$,
(EtO)$_3$Si—(CH$_2$)$_3$—S—(CH$_2$)$_3$—S—C(=O)—C$_6$H$_{13}$,
(EtO)$_3$Si—(CH$_2$)$_3$—S—(CH$_2$)$_3$—S—C(=O)—C$_7$H$_{15}$,
(EtO)$_3$Si—(CH$_2$)$_3$—S—(CH$_2$)$_3$—S—C(=O)—C$_9$H$_{19}$,
(EtO)$_3$Si—(CH$_2$)$_3$—S—(CH$_2$)$_3$—S—C(=O)—C$_{11}$H$_{23}$,
(EtO)$_3$Si—(CH$_2$)$_3$—S—(CH$_2$)$_3$—S—C(=O)—C$_{13}$H$_{27}$,
(EtO)$_3$Si—(CH$_2$)$_3$—S—(CH$_2$)$_3$—S—C(=O)—C$_{15}$H$_{31}$,
(EtO)$_3$Si—(CH$_2$)$_3$—S—(CH$_2$)$_3$—S—C(=O)—C$_{17}$H$_{35}$,
(EtO)$_3$Si—(CH$_2$)$_3$—S—(CH$_2$)$_6$—S—C(=O)—CH$_3$,
(EtO)$_3$Si—(CH$_2$)$_3$—S—(CH$_2$)$_6$—S—C(=O)—C$_2$H$_5$,
(EtO)$_3$Si—(CH$_2$)$_3$—S—(CH$_2$)$_6$—S—C(=O)—C$_3$H$_7$,
(EtO)$_3$Si—(CH$_2$)$_3$—S—(CH$_2$)$_6$—S—C(=O)—C$_4$H$_9$,
(EtO)$_3$Si—(CH$_2$)$_3$—S—(CH$_2$)$_6$—S—C(=O)—C$_5$H$_{11}$,
(EtO)$_3$Si—(CH$_2$)$_3$—S—(CH$_2$)$_6$—S—C(=O)—C$_6$H$_{13}$,
(EtO)$_3$Si—(CH$_2$)$_3$—S—(CH$_2$)$_6$—S—C(=O)—C$_7$H$_{15}$,
(EtO)$_3$Si—(CH$_2$)$_3$—S—(CH$_2$)$_6$—S—C(=O)—C$_9$H$_{19}$,
(EtO)$_3$Si—(CH$_2$)$_3$—S—(CH$_2$)$_6$—S—C(=O)—C$_{11}$H$_{23}$,
(EtO)$_3$Si—(CH$_2$)$_3$—S—(CH$_2$)$_6$—S—C(=O)—C$_{13}$H$_{27}$,
(EtO)$_3$Si—(CH$_2$)$_3$—S—(CH$_2$)$_6$—S—C(=O)—C$_{15}$H$_{31}$,
(EtO)$_3$Si—(CH$_2$)$_3$—S—(CH$_2$)$_6$—S—C(=O)—C$_{17}$H$_{35}$.

Especially preferred silanes are those of the formula I (EtO)$_3$Si—(CH$_2$)$_3$—S—(CH$_2$)$_6$—S—C(=O)—CH$_3$, (EtO)$_3$Si—(CH$_2$)$_3$—S—(CH$_2$)$_6$—S—C(=O)—C$_7$H$_{15}$ and (EtO)$_3$Si—(CH$_2$)$_3$—S—(CH$_2$)$_6$—S—C(=O)—C$_{17}$H$_{35}$.

Silanes of the formula II may preferably be:
(EtO)$_3$Si—CH$_2$—S—CH$_2$—S—CH$_2$—Si(OEt)$_3$,
(EtO)$_3$Si—(CH$_2$)$_2$—S—CH$_2$—S—(CH$_2$)$_2$—Si(OEt)$_3$,
(EtO)$_3$Si—(CH$_2$)$_3$—S—CH$_2$—S—(CH$_2$)$_3$—Si(OEt)$_3$,
(EtO)$_3$Si—CH$_2$—S—(CH$_2$)$_2$—S—CH$_2$—Si(OEt)$_3$,
(EtO)$_3$Si—(CH$_2$)$_2$—S—(CH$_2$)$_2$—S—(CH$_2$)$_2$—Si(OEt)$_3$,
(EtO)$_3$Si—(CH$_2$)$_3$—S—(CH$_2$)$_2$—S—(CH$_2$)$_3$—Si(OEt)$_3$,
(EtO)$_3$Si—CH$_2$—S—(CH$_2$)$_3$—S—CH$_2$—Si(OEt)$_3$,
(EtO)$_3$Si—(CH$_2$)$_2$—S—(CH$_2$)$_3$—S—(CH$_2$)$_2$—Si(OEt)$_3$,
(EtO)$_3$Si—(CH$_2$)$_3$—S—(CH$_2$)$_3$—S—(CH$_2$)$_3$—Si(OEt)$_3$,
(EtO)$_3$Si—CH$_2$—S—(CH$_2$)$_4$—S—CH$_2$—Si(OEt)$_3$,
(EtO)$_3$Si—(CH$_2$)$_2$—S—(CH$_2$)$_4$—S—(CH$_2$)$_2$—Si(OEt)$_3$,
(EtO)$_3$Si—(CH$_2$)$_3$—S—(CH$_2$)$_4$—S—(CH$_2$)$_3$—Si(OEt)$_3$,
(EtO)$_3$Si—CH$_2$—S—(CH$_2$)$_5$—S—CH$_2$—Si(OEt)$_3$,
(EtO)$_3$Si—(CH$_2$)$_2$—S—(CH$_2$)$_5$—S—(CH$_2$)$_2$—Si(OEt)$_3$,
(EtO)$_3$Si—(CH$_2$)$_3$—S—(CH$_2$)$_5$—S—(CH$_2$)$_3$—Si(OEt)$_3$,
(EtO)$_3$Si—CH$_2$—S—(CH$_2$)$_6$—S—CH$_2$—Si(OEt)$_3$,
(EtO)$_3$Si—(CH$_2$)$_2$—S—(CH$_2$)$_6$—S—(CH$_2$)$_2$—Si(OEt)$_3$,
(EtO)$_3$Si—(CH$_2$)$_3$—S—(CH$_2$)$_6$—S—(CH$_2$)$_3$—Si(OEt)$_3$.

An especially preferred silane is the silane of the formula II
(EtO)$_3$Si—(CH$_2$)$_3$—S—(CH$_2$)$_6$—S—(CH$_2$)$_3$—Si(OEt)$_3$.

Very particular preference is given to a silane mixture of
(EtO)$_3$Si—(CH$_2$)$_3$—(S—(CH$_2$)$_6$)$_n$—S—C(=O)—R$^5$ and
(EtO)$_3$Si—(CH$_2$)$_3$—S—(CH$_2$)$_6$—S—(CH$_2$)$_3$—Si(OEt)$_3$,
where n is 1.

An exceptionally preferred silane mixture is that of (EtO)$_3$Si—(CH$_2$)$_3$—S—(CH$_2$)$_6$—S—C(=O)—CH$_3$, (EtO)$_3$Si—(CH$_2$)$_3$—S—(CH$_2$)$_6$—S—C(=O)—C$_7$H$_{15}$ or (EtO)$_3$Si—(CH$_2$)$_3$—S—(CH$_2$)$_6$—S—C(=O)—C$_{17}$H$_{35}$ and (EtO)$_3$Si—(CH$_2$)$_3$—S—(CH$_2$)$_6$—S—(CH$_2$)$_3$—Si(OEt)$_3$.

The invention further provides a first process for preparing the silane mixture according to the invention, which is characterized in that the silane of the formula I

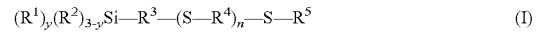

and a silane of the formula II

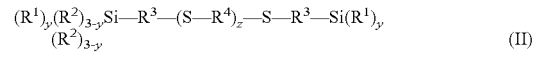

where R$^1$, R$^2$, R$^3$, R$^4$, R$^5$, n, y and z have the definition given above
are mixed in a molar ratio of 20:80-90:10, preferably 25:75-85:15, more preferably 25:75-80:20, most preferably 30:70-75:25.

Preferably, a silane of the formula I

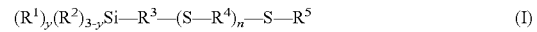

and a silane of the formula II

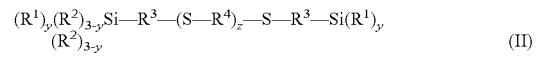

where R$^1$, R$^2$, R$^3$, R$^4$, R$^5$ and y have the definition given above and n is 1 and z=1 can be mixed.

The process according to the invention can be conducted with exclusion of air. The process according to the invention can be conducted under protective gas atmosphere, for example under argon or nitrogen, preferably under nitrogen.

The process according to the invention can be conducted at standard pressure, elevated pressure or reduced pressure. Preferably, the process according to the invention can be conducted at standard pressure.

Elevated pressure may be a pressure of 1.1 bar to 100 bar, preferably of 1.1 bar to 50 bar, more preferably of 1.1 bar to 10 bar and very preferably of 1.1 to 5 bar.

Reduced pressure may be a pressure of 1 mbar to 1000 mbar, preferably 250 mbar to 1000 mbar, more preferably 500 mbar to 1000 mbar.

The process according to the invention can be conducted between 20° C. and 100° C., preferably between 20° C. and 50° C., more preferably between 20° C. and 30° C.

The process according to the invention can be conducted in a solvent, for example methanol, ethanol, propanol, butanol, cyclohexanol, N,N-dimethylformamide, dimethyl sulfoxide, pentane, hexane, cyclohexane, heptane, octane, decane, toluene, xylene, acetone, acetonitrile, carbon tetrachloride, chloroform, dichloromethane, 1,2-dichloroethane, tetrachloroethylene, diethyl ether, methyl tert-butyl ether, methyl ethyl ketone, tetrahydrofuran, dioxane, pyridine or methyl acetate, or a mixture of the aforementioned solvents. The process according to the invention can preferably be conducted without solvent.

The invention further provides a process for producing the silane mixture according to the invention with n=1 and z=1, which is characterized in that
in a first step a mercaptosilane of the formula III $$(R^1)_y(R^2)_{3-y}Si—R^3—SH \qquad (III)$$

is reacted with a halogen compound of the formula IV $$Hal-R^4-Hal \qquad (IV)$$

where $R^1$, $R^2$, $R^3$ and $R^4$ have the definitions given above and Hal is F, Cl, Br or I, preferably Cl, in a molar ratio of the formula (II) to the formula (IV) of 34:66-76:24
and in a second step the product from the first process step is reacted with a salt of a thiocarboxylic acid of the formula (V)

$$NaS—C(=O)—R^5 \qquad (V)$$

where $R^5$ has the definition given above,
or, in the second step, the product from the first process step is reacted with NaSH and then an acid chloride of the formula (VI)

$$Cl—C(=O)—R^5 \qquad (VI)$$

where $R^5$ has the definition given above.

Mercaptosilanes of the formula III may preferably be:
$(C_2H_5O)_3Si—CH_2—SH$,
$(C_2H_5O)_3Si—CH_2CH_2—SH$,
$(C_2H_5O)_3Si—CH_2CH_2CH_2—SH$.

Halogen compounds of the formula IV may preferably be:
Cl—$CH_2$—Cl,
Cl—$CH_2CH_2$—Cl,
Cl—$CH_2CH_2CH_2$—Cl,
Cl—$CH_2CH_2CH_2CH_2$—Cl,
Cl—$CH_2CH_2CH_2CH_2CH_2$—Cl,
Cl—$CH_2$—$CH_2CH_2CH_2CH_2CH_2CH_2$—Cl,
Cl—$CH_2CH_2CH_2CH_2CH_2CH_2CH_2$—Cl or
Cl—$CH_2CH_2CH_2CH_2CH_2CH_2CH_2CH_2$—Cl.

Salts of a thiocarboxylic acid of the formula (V) may preferably be:
NaS—C(=O)—$CH_3$, NaS—C(=O)—$C_7H_{15}$ or NaS—C(=O)—$C_{17}H_{35}$.

Acid chlorides of the formula (VI) may preferably be:
Cl—C(=O)—$CH_3$, Cl—C(=O)—$C_7H_{15}$ or Cl—C(=O)—$C_{17}H_{35}$.

Especially preferably, the mercaptosilane of the formula III may be
$(EtO)_3Si—(CH_2)_3—SH$,
the halogen compound of the formula IV may be
Cl—$(CH_2)_6$—Cl,
and the thiocarboxylic acid of the formula V may be
NaS—C(=O)—$CH_3$, NaS—C(=O)—$C_7H_{15}$ or NaS—C(=O)—$C_{17}H_{35}$.
or the mercaptosilane of the formula III may be
$(EtO)_3Si—(CH_2)_3—SH$,
the halogen compound of the formula IV may be
Cl—$(CH_2)_6$—Cl,
and the acid chloride of the formula VI may be
Cl—C(=O)—$CH_3$, Cl—C(=O)—$C_7H_{15}$ or Cl—C(=O)—$C_{17}H_{35}$.

In the process for preparing the silane mixture according to the invention with n=1 and z=1, the first and second process steps can be effected in one reaction vessel by addition of all reactants.

In the first step of the process for preparing the silane mixture according to the invention with n=1 and z=1, the halogen compound of the formula IV can be metered into the mercaptosilane of the formula III.

In the first step of the process for preparing the silane mixture according to the invention with n=1 and z=1, the mercaptosilane of the formula III can preferably be metered into the halogen compound of the formula IV.

The reaction in the first step of the process for preparing the silane mixture according to the invention with n=1 and z=1 can be conducted with exclusion of air.

The reaction in the first step of the process for preparing the silane mixture according to the invention with n=1 and z=1 can be conducted under protective gas atmosphere, for example under argon or nitrogen, preferably under nitrogen.

The first step of the process for preparing the silane mixture according to the invention with n=1 and z=1 can be conducted at standard pressure, elevated pressure or reduced pressure. Preferably, the process according to the invention can be conducted at standard pressure. Elevated pressure may be a pressure of 1.1 bar to 100 bar, preferably of 1.1 bar to 50 bar, more preferably of 1.1 bar to 10 bar and very preferably of 1.1 to 5 bar.

Reduced pressure may be a pressure of 1 mbar to 1000 mbar, preferably 250 mbar to 1000 mbar, more preferably 500 mbar to 1000 mbar.

The first step of the process for preparing the silane mixture according to the invention with n=1 and z=1 can be conducted between 0° C. and 150° C., preferably between 30° C. and 100° C., more preferably between 60° C. and 80° C.

The reaction in the first step of the process for preparing the silane mixture according to the invention with n=1 and z=1 can be conducted without solvent or in a solvent, for example methanol, ethanol, propanol, butanol, cyclohexanol, N,N-dimethylformamide, dimethyl sulfoxide, pentane, hexane, cyclohexane, heptane, octane, decane, toluene, xylene, acetone, acetonitrile, carbon tetrachloride, chloroform, dichloromethane, 1,2-dichloroethane, tetrachloroethylene, diethyl ether, methyl tert-butyl ether, methyl ethyl ketone, tetrahydrofuran, dioxane, pyridine, ethyl acetate or a mixture of the aforementioned solvents. The solvent may preferably be dichloromethane, ethanol, methyl tert-butyl ether, toluene, ethyl acetate, pentane, hexane or a mixture of the aforementioned solvents.

The reaction in the first step of the process for preparing the silane mixture according to the invention with n=1 and z=1 can be conducted without organic solvents. The solvent may be water.

The reaction product from the first step of the process for preparing the silane mixture according to the invention with n=1 and z=1 can subsequently be freed of solid by-products by filtration.

The solvent in the first step of the process for preparing the silane mixture according to the invention with n=1 and z=1 can subsequently be removed, preferably distilled off.

The reaction in the second step of the process for preparing the silane mixture according to the invention with n=1 and z=1 can be conducted with exclusion of air.

The reaction in the second step of the process for preparing the silane mixture according to the invention with n=1 and z=1 can be conducted under protective gas atmosphere, for example under argon or nitrogen, preferably under nitrogen.

The second step of the process for preparing the silane mixture according to the invention with n=1 and z=1 can be conducted at standard pressure, elevated pressure or reduced pressure. Preferably, the process according to the invention can be conducted at standard pressure. Elevated pressure may be a pressure of 1.1 bar to 100 bar, preferably of 1.1 bar to 50 bar, more preferably of 1.1 bar to 10 bar and very preferably of 1.1 to 5 bar.

Reduced pressure may be a pressure of 1 mbar to 1000 mbar, preferably 250 mbar to 1000 mbar, more preferably 500 mbar to 1000 mbar.

The second step of the process for preparing the silane mixture according to the invention with n=1 and z=1 can be conducted between 20° C. and 150° C., preferably between 40° C. and 100° C., more preferably between 60° C. and 90° C.

The reaction in the second step of the process for preparing the silane mixture according to the invention with n=1 and z=1 can be conducted without solvent or in a solvent, for example methanol, ethanol, propanol, butanol, cyclohexanol, N,N-dimethylformamide, dimethyl sulfoxide, pentane, hexane, cyclohexane, heptane, octane, decane, toluene, xylene, acetone, acetonitrile, carbon tetrachloride, chloroform, dichloromethane, 1,2-dichloroethane, tetrachloroethylene, diethyl ether, methyl tert-butyl ether, methyl ethyl ketone, tetrahydrofuran, dioxane, pyridine or ethyl acetate. The solvent may preferably be ethanol.

The reaction in the second step of the process for preparing the silane mixture according to the invention with n=1 and z=1 can be conducted without organic solvents. The solvent may be water.

The reaction in the second step of the process for preparing the silane mixture according to the invention with n=1 and z=1 can be conducted in water in the presence of phase transfer catalysts and optionally with addition of salts and/or buffers.

The solvent in the second step of the process for preparing the silane mixture according to the invention with n=1 and z=1 can subsequently be removed, preferably distilled off.

The reaction product in the second step of the process for preparing the silane mixture according to the invention with n=1 and z=1 after the filtration and removal of solvent, can be dried. The drying can be effected at temperatures of 20° C.-100° C., preferably of 25° C.-50° C. The drying can be effected at a reduced pressure of 1-500 mbar.

The silane mixture according to the invention can be used as adhesion promoter between inorganic materials, for example glass beads, glass flakes, glass surfaces, glass fibres, or oxidic fillers, preferably silicas such as precipitated silicas and fumed silicas, and organic polymers, for example thermosets, thermoplastics or elastomers, or as crosslinking agents and surface modifiers for oxidic surfaces.

The silane mixture according to the invention can be used as coupling reagents in filled rubber mixtures, examples being tyre treads, industrial rubber articles or footwear soles.

Advantages of the silane mixtures according to the invention are reduced rolling resistance and improved resolution of the trade-off between rolling resistance and wet grip in rubber mixtures.

EXAMPLES

NMR method: The molar ratios and proportions by mass reported as analysis results in the examples come from $^{13}$C NMR measurements with the following indices: 100.6 MHz, 1000 scans, solvent: $CDCl_3$, internal standard for calibration: tetramethylsilane, relaxation aid: $Cr(acac)_3$; for the determination of the proportion by mass in the product, a defined amount of dimethyl sulfone was added as internal standard and the molar ratios of the products were used to calculate the proportion by mass.

Comparative Example 1:
3-octanoylthio-1-propyltriethoxysilane, NXT Silane from Momentive Performance Materials.

Comparative Example 2: bistriethoxysilyloctane from ABCR GmbH.

Comparative Example 3

6.84 parts by weight of Comparative Example 1 together with 1.65 parts by weight of Comparative Example 2 were weighed into a flat PE bag and mixed. This mixture corresponds to a molar ratio: 83% $(EtO)_3Si(CH_2)_3SCO(CH_2)_6CH_3$ and 17% $(EtO)_3Si(CH_2)_8Si(OEt)_3$.

Comparative Example 4

6.84 parts by weight of Comparative Example 1 together with 2.47 parts by weight of Comparative Example 2 were weighed into a flat PE bag and mixed. This mixture corresponds to a molar ratio: 77% $(EtO)_3Si(CH_2)_3SCO(CH_2)_6CH_3$ and 23% $(EtO)_3Si(CH_2)_8Si(OEt)_3$.

Comparative Example 5

6.84 parts by weight of Comparative Example 1 together with 3.29 parts by weight of Comparative Example 2 were weighed into a flat PE bag and mixed. This mixture corresponds to a molar ratio: 71% $(EtO)_3Si(CH_2)_3SCO(CH_2)_6CH_3$ and 29% $(EtO)_3Si(CH_2)_8Si(OEt)_3$.

Comparative Example 6

6.30 parts by weight of Comparative Example 1 together with 2.53 parts by weight of Comparative Example 2 were weighed into a flat PE bag and mixed. This mixture corresponds to a molar ratio: 75% $(EtO)_3Si(CH_2)_3SCO(CH_2)_6CH_3$ and 25% $(EtO)_3Si(CH_2)_8Si(OEt)_3$.

Comparative Example 7

4.20 parts by weight of Comparative Example 1 together with 3.79 parts by weight of Comparative Example 2 were weighed into a flat PE bag and mixed. This mixture corresponds to a molar ratio: 57% $(EtO)_3Si(CH_2)_3SCO(CH_2)_6CH_3$ and 43% $(EtO)_3Si(CH_2)Si(OEt)_3$.

Comparative Example 8

2.10 parts by weight of Comparative Example 1 together with 5.06 parts by weight of Comparative Example 2 were weighed into a flat PE bag and mixed. This mixture corresponds to a molar ratio: 33% $(EtO)_3Si(CH_2)_3SCO(CH_2)_6CH_3$ and 67% $(EtO)_3Si(CH_2)_8Si(OEt)_3$.

Comparative Example 9:
1-chloro-6-thiopropyltriethoxysilylhexane

NaOEt (21% in EtOH; 1562 g; 4.820 mol) was metered into mercaptopropyltriethoxysilane (1233 g; 5.170 mol) over the course of 1 h while stirring at room temperature. On completion of addition, the reaction mixture was heated at reflux for 2 h and then left to cool to room temperature. The intermediate formed was metered into 1,6-dichlorohexane (4828 g; 31.14 mol) that had been heated to 80° C. over the course of 30 min. On completion of addition, the reaction mixture was heated at reflux for 3 h, before being left to cool to room temperature. The reaction mixture was filtered and the filtercake was rinsed with EtOH. The volatile constituents were removed under reduced pressure and the 1-chloro-6-thiopropyltriethoxysilylhexane intermediate (yield: 89%, molar ratio: 97% 1-chloro-6-thiopropyltriethoxysilylhexane, 3% bis(thiopropyltriethoxysilyl)hexane; % by weight: 95% by weight of 1-chloro-6-thiopropyltriethoxysilylhexane, 5% by weight of 1,6-bis(thiopropyltriethoxysilyl)hexane) was obtained as a colourless to brown liquid.

Comparative Example 10: S-(6-((3-(triethoxysilyl)propyl)thio)hexy) thioacetate $Na_2CO_3$ (59.78 g; 0.564 mol) and an aqueous solution of NaSH (40% in water; 79.04 g; 0.564 mol) were initially charged together with water (97.52 g). Then tetrabutylphosphonium bromide (TBPB) (50% in water; 3.190 g; 0.005 mol) was added and acetyl chloride (40.58 g; 0.517 mol) was added dropwise over the course of 1 h, during which the reaction temperature was kept at 25-32° C. On completion of addition of the acetyl chloride, the mixture was stirred at room temperature for 1 h. Then TBPB (50% in water; 3.190 g; 0.005 mol) and 1-chloro-6-thiopropyltriethoxysilylhexane (from Comparative Example 9; 167.8 g; 0.470 mol) were added and the mixture was heated at reflux for 3-5 h. The progress of the reaction was monitored by means of gas chromatography. Once the 1-chloro-6-thiopropyltriethoxysilylhexane had reacted to an extent of >96%, water was added until all the salts had dissolved and the phases were separated. The volatile constituents of the organic phase were removed under reduced pressure, and S-(6-((3-(triethoxysilyl)propyl)thio)hexyl) thioacetate (yield: 90%, molar ratio: 97% S-(6-((3-(triethoxysilyl)propyl)thio)hexyl) thioacetate, 3% bis(thiopropyltriethoxysilyl)hexane; % by weight: 96% by weight of S-(6-((3-(triethoxysilyl)propyl)thio)hexyl) thioacetate, 4% of 1,6-bis(thiopropyltriethoxysilyl)hexane) was obtained as a yellow to brown liquid.

Comparative Example 11: S-(6-((3-(triethoxysilyl)propyl)thio)hexyl) thiooctanoate $Na_2CO_3$ (220.2 g; 2.077 mol) and an aqueous solution of NaSH (40% in water; 291.2 g; 2.077 mol) were initially charged together with water (339.2 g). Then tetrabutylammonium bromide (TBAB) (50% in water; 10.96 g; 0.017 mol) was added and octanoyl chloride (307.2 g; 1.889 mol) was added dropwise over the course of 2.5 h, during which the reaction temperature was kept at 24-28° C. On completion of addition of the octanoyl chloride, the mixture was stirred at room temperature for 1 h. Then TBAB (50% in water; 32.88 g; 0.051 mol) and 1-chloro-6-thiopropyltriethoxysilylhexane (from Comparative Example 9, 606.9 g; 1.700 mol) were added and the mixture was heated at reflux for 10 h. Then water was added until all the salts had dissolved and the phases were separated. The volatile constituents of the organic phase were removed under reduced pressure, and S-(6-((3-(triethoxysilyl)propyl)thio)hexyl) thiooctanoate (yield: 95%, molar ratio: 97% S-(6-((3-(triethoxysilyl)propyl)thio)hexyl) thiooctanoate, 3% bis(thiopropyltriethoxysilyl)hexane; % by weight: 96% by weight of S-(6-((3-(triethoxysilyl)propyl)thio)hexyl) thiooctanoate, 4% by weight of 1,6-bis(thiopropyltriethoxysilyl)hexane) was obtained as a yellow to brown liquid.

Comparative Example 12: S-(6-((3-(triethoxysilyl)propyl)thio)hexyl) thiooctadecanoate S-(6-((3-(Triethoxysilyl)propyl)thio)hexyl) thiooctadecanoate was prepared from 1-chloro-6-thiopropyltriethoxysilylhexane (from Comparative Example 9) in accordance with Synthesis Examples 1 and 3 in JP2012149189.

S-(6-((3-(Triethoxysilyl)propyl)thio)hexyl) thiooctadecanoate (yield: 89%, molar ratio: 97% S-(6-((3-(triethoxysilyl)propyl)thio)hexyl) thiooctadecanoate, 3% bis(thiopropyltriethoxysilyl)hexane; % by weight: 97% by weight of S-(6-((3-(triethoxysilyl)propyl)thio)hexyl) thiooctadecanoate, 3% by weight of 1,6-bis(thiopropyltriethoxysilyl)hexane) was obtained as a yellow to brown liquid.

Comparative Example 13: 1,6-bis(thiopropyltriethoxysilyl)hexane

Sodium ethoxide (21% in EtOH; 82.3 g; 0.254 mol; 2.05 eq) was metered into mercaptopropyltriethoxysilane (62.0 g; 0.260 mol; 2.10 eq) such that the reaction temperature did not exceed 35° C. On completion of addition, the mixture was heated at reflux for 2 h. Then the reaction mixture was added to 1,6-dichlorohexane (19.2 g; 0.124 mol; 1.00 eq) at 80° C. over 1.5 h. On completion of addition, the mixture was heated at reflux for 3 h and then left to cool to room temperature. Precipitated salts were filtered off and the product was freed of the solvent under reduced pressure. The product (yield: 88%, purity: >99% in $^{13}C$ NMR) was obtained as a clear liquid.

Example 1

6.84 parts by weight of Comparative Example 11 together with 1.59 parts by weight of Comparative Example 13 were weighed into a flat PE bag and mixed. This mixture corresponds to a molar ratio: Silane of the formula I: 80% $(EtO)_3Si(CH_2)_3S(CH_2)_6SCO(CH_2)_6CH_3$ and silane of the formula II: 20% $(EtO)_3Si(CH_2)_3S(CH_2)_6S(CH_2)_3Si(OEt)_3$.

Example 2

6.84 parts by weight of Comparative Example 11 together with 2.39 parts by weight of Comparative Example 13 were weighed into a flat PE bag and mixed. This mixture corresponds to a molar ratio: Silane of the formula I: 74% $(EtO)_3Si(CH_2)_3S(CH_2)_6SCO(CH_2)_6CH_3$ and silane of the formula II: 26% $(EtO)_3Si(CH_2)_3S(CH_2)_6S(CH_2)_3Si(OEt)_3$.

Example 3

6.84 parts by weight of Comparative Example 11 together with 3.18 parts by weight of Comparative Example 13 were weighed into a flat PE bag and mixed. This mixture corresponds to a molar ratio: Silane of the formula I: 69% $(EtO)_3Si(CH_2)_3S(CH_2)_6SCO(CH_2)_6CH_3$ and silane of the formula II: 31% $(EtO)_3Si(CH_2)_3S(CH_2)_6S(CH_2)_3Si(OEt)_3$.

Example 4

8.31 parts by weight of Comparative Example 11 together with 3.22 parts by weight of Comparative Example 13 were weighed into a flat PE bag and mixed. This mixture corresponds to a molar ratio: Silane of the formula I: 72%

(EtO)₃Si(CH₂)₃S(CH₂)₆SCO(CH₂)₆CH₃ and silane of the formula II: 28% (EtO)₃Si(CH₂)₃S(CH₂)₆S(CH₂)₃Si(OEt)₃.

Example 5

5.54 parts by weight of Comparative Example 11 together with 4.83 parts by weight of Comparative Example 13 were weighed into a flat PE bag and mixed. This mixture corresponds to a molar ratio: Silane of the formula I: 55% (EtO)₃Si(CH₂)₃S(CH₂)₆SCO(CH₂)₆CH₃ and silane of the formula II: 45% (EtO)₃Si(CH₂)₃S(CH₂)₆S(CH₂)₃Si(OEt)₃.

Example 6

2.77 parts by weight of Comparative Example 11 together with 6.44 parts by weight of Comparative Example 13 were weighed into a flat PE bag and mixed. This mixture corresponds to a molar ratio: Silane of the formula I: 32% (EtO)₃Si(CH₂)₃S(CH₂)₆SCO(CH₂)₆CH₃ and silane of the formula II: 68% (EtO)₃Si(CH₂)₃S(CH₂)₆S(CH₂)₃Si(OEt)₃.

Example 7

6.86 parts by weight of Comparative Example 10 together with 3.22 parts by weight of Comparative Example 13 were weighed into a flat PE bag and mixed. This mixture corresponds to a molar ratio: Silane of the formula I: 73% (EtO)₃Si(CH₂)₃S(CH₂)₆SCOCH₃ and silane of the formula II: 27% (EtO)₃Si(CH₂)₃S(CH₂)₆S(CH₂)₃Si(OEt)₃.

Example 8

4.57 parts by weight of Comparative Example 10 together with 4.83 parts by weight of Comparative Example 13 were weighed into a flat PE bag and mixed. This mixture corresponds to a molar ratio: Silane of the formula I: 55% (EtO)₃Si(CH₂)₃S(CH₂)₆SCOCH₃ and silane of the formula II: 45% (EtO)₃Si(CH₂)₃S(CH₂)₆S(CH₂)₃Si(OEt)₃.

Example 9

2.29 parts by weight of Comparative Example 10 together with 6.44 parts by weight of Comparative Example 13 were weighed into a flat PE bag and mixed. This mixture corresponds to a molar ratio: Silane of the formula I: 32% (EtO)₃Si(CH₂)₃S(CH₂)₆SCOCH₃ and silane of the formula II: 68% (EtO)₃Si(CH₂)₃S(CH₂)₆S(CH₂)₃Si(OEt)₃.

Example 10

9.14 parts by weight of Comparative Example 10 together with 1.61 parts by weight of Comparative Example 13 were weighed into a flat PE bag and mixed. This mixture corresponds to a molar ratio: Silane of the formula I: 86% (EtO)₃Si(CH₂)₃S(CH₂)₆SCOCH₃ and silane of the formula II: 14% (EtO)₃Si(CH₂)₃S(CH₂)₆S(CH₂)₃Si(OEt)₃.

Example 11

11.08 parts by weight of Comparative Example 10 together with 1.61 parts by weight of Comparative Example 13 were weighed into a flat PE bag and mixed. This mixture corresponds to a molar ratio: Silane of the formula I: 89% (EtO)₃Si(CH₂)₃S(CH₂)₆SCO(CH₂)₆CH₃ and silane of the formula II: 11% (EtO)₃Si(CH₂)₃S(CH₂)₆S(CH₂)₃Si(OEt)₃.

Example 12

14.32 parts by weight of Comparative Example 10 together with 1.61 parts by weight of Comparative Example 13 were weighed into a flat PE bag and mixed. This mixture corresponds to a molar ratio: Silane of the formula I: 89% (EtO)₃Si(CH₂)₃S(CH₂)₆SCO(CH₂)₁₆CH₃ and silane of the formula II: 11% (EtO)₃Si(CH₂)₃S(CH₂)₆S(CH₂)₃Si(OEt)₃.

Example 13

1-chloro-6-thiopropyltriethoxysilylhexane and 1,6-bis (thiopropyltriethoxysilyl)hexane NaOEt (21% in EtOH; 1562 g; 4.820 mol) was metered into mercaptopropyltriethoxysilane (1233 g; 5.170 mol) over the course of 1 h while stirring at room temperature. On completion of addition, the reaction mixture was heated at reflux for 2 h and then left to cool to room temperature. The intermediate formed was metered into 1,6-dichlorohexane (801.7 g; 5.170 mol) that had been heated to 80° C. over the course of 30 min. On completion of addition, the reaction mixture was heated at reflux for 3 h, before being left to cool to room temperature. The reaction mixture was filtered and the filtercake was rinsed with EtOH. The volatile constituents were removed under reduced pressure and the 1-chloro-6-thiopropyltriethoxysilylhexane intermediate (yield: 88%, molar ratio: 66% 1-chloro-6-thiopropyltriethoxysilylhexane, 34% bis(thiopropyltriethoxysilyl)hexane; % by weight: 56% by weight of 1-chloro-6-thiopropyltriethoxysilylhexane, 44% by weight of 1,6-bis(thiopropyltriethoxysilyl)hexane) was obtained.

Example 14: S-(6-((3-(triethoxysilyl)propyl)thio) hexyl) thioacetate and 1,6-bis(thiopropyltriethoxysilyl)hexane The synthesis was conducted as in Comparative Example 2. However, rather than the 1-chloro-6-thiopropyltriethoxysilylhexane from Comparative Example 9, the equimolar amount of the material from Example 13 was used.

S-(6-((3-(Triethoxysilyl)propyl)thio)hexyl) thioacetate (yield: 98%, molar ratio: 69% S-(6-((3-(triethoxysilyl)propyl)thio)hexyl) thioacetate, 31% bis(thiopropyltriethoxysilyl)hexane; % by weight: 61% by weight of S-(6-((3-(triethoxysilyl)propyl)thio)hexyl) thioacetate, 39% by weight of 1,6-bis(thiopropyltriethoxysilyl)hexane) was obtained as a yellow to brown liquid.

Example 15: S-(6-((3-(triethoxysilyl)propyl)thio) hexyl) thiooctanoate and 1,6-bis(thiopropyltriethoxysilyl)hexane The synthesis was conducted as in Comparative Example 3. However, rather than the 1-chloro-6-thiopropyltriethoxysilylhexane from Comparative Example 9, the equimolar amount of the material from Example 13 was used.

S-(6-((3-(Triethoxysilyl)propyl)thio)hexyl) thiooctanoate (yield: 99%, molar ratio: 68% S-(6-((3-(triethoxysilyl)propyl)thio)hexyl) thiooctanoate, 32% bis(thiopropyltriethoxysilyl)hexane; % by weight: 65% by weight of S-(6-((3-(triethoxysilyl)propyl)thio)hexyl) thiooctanoate, 35% by weight of 1,6-bis(thiopropyltriethoxysilyl)hexane) was obtained as a yellow to brown liquid.

Example 16: S-(6-((3-(triethoxysilyl)propyl)thio) hexyl) thiooctadecanoate and 1,6-bis(thiopropyltriethoxysilyl)hexane The synthesis was conducted as in Comparative Example 4. However, rather than the 1-chloro-6-thiopropyltriethoxysilylhexane from Comparative Example 9, the equimolar amount of the material from Example 13 was used.

S-(6-((3-(Triethoxysilyl)propyl)thio)hexyl) thiooctadecanoate (yield: 87%, molar ratio: 67% S-(6-((3-(triethoxysilyl)propyl)thio)hexyl) thiooctadecanoate, 33% bis(thiopropyltriethoxysilyl)hexane; % by weight: 69% by weight of S-(6-((3-(triethoxysilyl)propyl)thio)hexyl) thiooctadecanoate, 31% by weight of 1,6-bis(thiopropyltriethoxysilyl)hexane) was obtained as a yellow to brown liquid.

Example 17: Rubber Tests

The formulation used for the rubber mixtures is specified in Table 1 below. The unit phr means parts by weight based on 100 parts of the raw rubber used.

TABLE 1

| | Mixture 1/ phr | Mixture 2/ phr | Mixture 3/ phr | Mixture 4/ phr | Mixture 5/ phr | Mixture 6/ phr | Mixture 7/ phr | Mixture 8/ phr | Mixture 9/ phr | Mixture 10/ phr | Mixture 11/ phr Inv. | Mixture 12/ phr Inv. | Mixture 13/ phr Inv | Mixture 14/ phr Inv. | Mixture 15/ phr Inv. | Mixture 16/ phr Inv. | Mixture 17/ phr Inv. | Mixture 18/ phr Inv. | Mixture 19/ phr Inv. |
|---|---|---|---|---|---|---|---|---|---|---|---|---|---|---|---|---|---|---|---|
| 1st stage | | | | | | | | | | | | | | | | | | | |
| NR[a] | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| BR[b] | 18.0 | 18.0 | 18.0 | 18.0 | 18.0 | 18.0 | 18.0 | 18.0 | 18.0 | 18.0 | 18.0 | 18.0 | 18.0 | 18.0 | 18.0 | 18.0 | 18.0 | 18.0 | 18.0 |
| S-SBR[c] | 72.0 | 72.0 | 72.0 | 72.0 | 72.0 | 72.0 | 72.0 | 72.0 | 72.0 | 72.0 | 72.0 | 72.0 | 72.0 | 72.0 | 72.0 | 72.0 | 72.0 | 72.0 | 72.0 |
| Silica[d] | 95.0 | 95.0 | 95.0 | 95.0 | 95.0 | 95.0 | 95.0 | 95.0 | 95.0 | 95.0 | 95.0 | 95.0 | 95.0 | 95.0 | 95.0 | 95.0 | 95.0 | 95.0 | 95.0 |
| TDAE oil[e] | 50.0 | 50.0 | 50.0 | 50.0 | 50.0 | 50.0 | 50.0 | 50.0 | 50.0 | 50.0 | 50.0 | 50.0 | 50.0 | 50.0 | 50.0 | 50.0 | 50.0 | 50.0 | 50.0 |
| 6PPD[f] | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Antiozonant wax | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Zinc oxide | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| Stearic acid | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| Comp. Ex. 3 | 8.5 | | | | | | | | | | | | | | | | | | |
| Comp. Ex. 4 | | 9.3 | | | | | | | | | | | | | | | | | |
| Comp. Ex. 5 | | | 10.1 | | | | | | | | | | | | | | | | |
| Comp. Ex. 6 | | | | 8.8 | | | | | | | | | | | | | | | |
| Comp. Ex. 7 | | | | | 8.0 | | | | | | | | | | | | | | |
| Comp. Ex. 8 | | | | | | 7.2 | | | | | | | | | | | | | |
| Comp. Ex. 10 | | | | | | | 6.8 | | | | | | | | | | | | |
| Comp. Ex. 11 | | | | | | | | 6.8 | | | | | | | | | | | |
| Comp. Ex. 12 | | | | | | | | | 6.8 | | | | | | | | | | |
| Comp. Ex. 13 | | | | | | | | | | 6.8 | | | | | | | | | |
| Example 1 | | | | | | | | | | | 8.4 | | | | | | | | |
| Example 2 | | | | | | | | | | | | 9.2 | | | | | | | |
| Example 3 | | | | | | | | | | | | | 10.0 | | | | | | |
| Example 4 | | | | | | | | | | | | | | 11.5 | | | | | |
| Example 5 | | | | | | | | | | | | | | | 10.4 | | | | |
| Example 6 | | | | | | | | | | | | | | | | 9.21 | | | |
| Example 7 | | | | | | | | | | | | | | | | | 10.0 | | |
| Example 8 | | | | | | | | | | | | | | | | | | 9.4 | |
| Example 9 | | | | | | | | | | | | | | | | | | | 8.7 |
| 2nd stage Stage 1 batch | | | | | | | | | | | | | | | | | | | |
| 3rd stage Stage 2 batch | | | | | | | | | | | | | | | | | | | |
| DPG[g] | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| CBS[h] | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Sulfur[i] | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |

Substances Used:
a) NR TSR: natural rubber (TSR=technically specified rubber).
b) Europrene Neocis BR 40, from Polimeri.
c) S—SBR: Sprintan® SLR-4601, from Trinseo.
d) Silica: ULTRASIL® VN 3 GR from Evonik Industries AG (precipitated silica, BET surface area=175 m²/g).
e) TDAE oil: TDAE=treated distillate aromatic extract.
f) 6PPD: N-(1,3-dimethylbutyl)-N'-phenyl-p-phenylenediamine (6PPD).
g) DPG: N,N'-diphenylguanidine (DPG).
h) CBS: N-cyclohexyl-2-benzothiazolesulfenamide.
i) Sulfur: ground sulfur.

The mixture was produced in processes customary in the rubber industry in three stages in a laboratory mixer of capacity 300 millilitres to 3 litres, by first mixing, in the first mixing stage (base mixing stage), all the constituents apart from the vulcanization system (sulfur and vulcanization-influencing substances) at 145 to 165° C., target temperatures of 152 to 157° C., for 200 to 600 seconds. In the second stage, the mixture from stage 1 was thoroughly mixed once more, performing what is called a remill. Addition of the vulcanization system in the third stage (ready-mix stage) produced the finished mixture, with mixing at 90 to 120° C. for 180 to 300 seconds. All the mixtures were used to produce test specimens by vulcanization under pressure at 160° C. after t95 (measured on a moving die rheometer to ASTM D 5289-12/ISO 6502).

The general process for producing rubber mixtures and vulcanizates thereof is described in "Rubber Technology Handbook", W. Hofmann, Hanser Verlag 1994.

Rubber testing was effected in accordance with the test method specified in Table 2. The results of the rubber testing are reported in Table 3.

TABLE 2

| Physical testing | Standard/conditions |
| --- | --- |
| Rebound resilience at 23° C. and 70° C. (%) | ISO 8307 (fall height 500 mm, steel ball d = 19 mm, 28 g) |

TABLE 3

| | Mixture 1 | Mixture 2 | Mixture 3 | Mixture 4 | Mixture 5 |
| --- | --- | --- | --- | --- | --- |
| Rebound resilience at 23° C./% | 20.2 | 20.2 | 20.2 | 19.8 | 19.7 |
| Rebound resilience at 70° C./% | 38.6 | 38.4 | 39.2 | 38.0 | 37.2 |
| (Rebound resilience at 70° C./%) − (rebound resilience at 23° C./%) | 18.4 | 18.1 | 19.0 | 18.2 | 17.5 |

| | Mixture 6 | Mixture 7 | Mixture 8 | Mixture 9 | Mixture 10 |
| --- | --- | --- | --- | --- | --- |
| Rebound resilience at 23° C./% | 19.8 | 26.1 | 26.2 | 27.1 | 21.3 |
| Rebound resilience at 70° C./% | 37.0 | 39.8 | 39.9 | 38.8 | 39.6 |
| (Rebound resilience at 70° C./%) − (rebound resilience at 23° C./%) | 17.2 | 13.7 | 13.6 | 11.7 | 18.3 |

| | Mixture 11 Inv. | Mixture 12 Inv. | Mixture 13 Inv. | Mixture 14 Inv. | Mixture 15 Inv. |
| --- | --- | --- | --- | --- | --- |
| Rebound resilience at 23° C./% | 26.2 | 26.1 | 26.3 | 26.8 | 25.6 |
| Rebound resilience at 70° C./% | 45.9 | 47.2 | 47.3 | 49.4 | 48.2 |
| (Rebound resilience at 70° C./%) − (rebound resilience at 23° C./%) | 19.7 | 21.1 | 21.0 | 22.6 | 22.5 |

| | Mixture 16 Inv. | Mixture 17 Inv. | Mixture 18 Inv. | Mixture 19 Inv. |
| --- | --- | --- | --- | --- |
| Rebound resilience at 23° C./% | 23.8 | 26.6 | 25.8 | 24.5 |
| Rebound resilience at 70° C./% | 45.8 | 46.6 | 46.5 | 45.7 |
| (Rebound resilience at 70° C./%) − (rebound resilience at 23° C./%) | 22.0 | 20.1 | 20.7 | 21.2 |

Compared to the comparative mixtures, the mixtures according to the invention feature improved rolling resistance (rebound resilience measured at 70° C.). Moreover, the silane mixtures according to the invention lead to an advantageous resolution of the trade-off between rolling resistance and wet grip (difference in rebound resilience measured at 70° C. and at 23° C.).

Example 18: Rubber Tests

The formulation used for the rubber mixtures is specified in Table 1 below. The unit phr means parts by weight based on 100 parts of the raw rubber used.

TABLE 4

| | Mixture 7/ phr | Mixture 8/ phr | Mixture 9/ phr | Mixture 10/ phr | Mixture 20/ phr Inv. | Mixture 21/ phr Inv. | Mixture 22/ phr Inv. |
| --- | --- | --- | --- | --- | --- | --- | --- |
| 1st stage | | | | | | | |
| BR[b] | 10.0 | 10.0 | 10.0 | 10.0 | 10.0 | 10.0 | 10.0 |
| S-SBR[c] | 18.0 | 18.0 | 18.0 | 18.0 | 18.0 | 18.0 | 18.0 |
| Silica[d] | 72.0 | 72.0 | 72.0 | 72.0 | 72.0 | 72.0 | 72.0 |
| TDAE oil[e] | 95.0 | 95.0 | 95.0 | 95.0 | 95.0 | 95.0 | 95.0 |
| 6PPD[f] | 50.0 | 50.0 | 50.0 | 50.0 | 50.0 | 50.0 | 50.0 |
| Antiozonant wax | 2.0 | 2.0 | 2.0 | 2.0 | 2.0 | 2.0 | 2.0 |
| Zinc oxide | 2.0 | 2.0 | 2.0 | 2.0 | 2.0 | 2.0 | 2.0 |
| Stearic acid | 2.5 | 2.5 | 2.5 | 2.5 | 2.5 | 2.5 | 2.5 |
| Comp. Ex. 10 | 6.8 | | | | | | |
| Comp. Ex. 11 | | 6.8 | | | | | |
| Comp. Ex. 12 | | | 6.8 | | | | |

TABLE 4-continued

| | Mixture 7/ phr | Mixture 8/ phr | Mixture 9/ phr | Mixture 10/ phr | Mixture 20/ phr Inv. | Mixture 21/ phr Inv. | Mixture 22/ phr Inv. |
| --- | --- | --- | --- | --- | --- | --- | --- |
| Comp. Ex. 13 | | | | 6.8 | | | |
| Example 10 | | | | | 10.7 | | |
| Example 11 | | | | | | 12.7 | |
| Example 12 | | | | | | | 15.9 |
| 2nd stage Stage 1 batch 3rd stage | | | | | | | |

TABLE 4-continued

|  | Mixture 7/ phr | Mixture 8/ phr | Mixture 9/ phr | Mixture 10/ phr | Mixture 20/ phr Inv. | Mixture 21/ phr Inv. | Mixture 22/ phr Inv. |
|---|---|---|---|---|---|---|---|
| Stage 2 batch | | | | | | | |
| DPG[g] | 2.0 | 2.0 | 2.0 | 2.0 | 2.0 | 2.0 | 2.0 |
| CBS[h] | 2.0 | 2.0 | 2.0 | 2.0 | 2.0 | 2.0 | 2.0 |
| Sulfur[i] | 2.0 | 2.0 | 2.0 | 2.0 | 2.0 | 2.0 | 2.0 |

Substances used:
[a] NR TSR: natural rubber (TSR = technically specified rubber).
[b] Europrene Neocis BR 40, from Polimeri.
[c] S-SBR: Sprintan ® SLR-4601, from Trinseo.
[d] Silica: ULTRASIL ® VN 3 GR from Evonik Industries AG (precipitated silica, BET surface area = 175 m²/g).
[e] TDAE oil: TDAE = treated distillate aromatic extract.
[f] 6PPD: N-(1,3-dimethylbutyl)-N'-phenyl-p-phenylenediamine (6PPD).
[g] DPG: N,N'-diphenylguanidine (DPG).
[h] CBS: N-cyclohexyl-2-benzothiazolesulfenamide.
[i] Sulfur: ground sulfur.

The mixture was produced in processes customary in the rubber industry in three stages in a laboratory mixer of capacity 300 millilitres to 3 litres, by first mixing, in the first mixing stage (base mixing stage), all the constituents apart from the vulcanization system (sulfur and vulcanization-influencing substances) at 145 to 165° C., target temperatures of 152 to 157° C., for 200 to 600 seconds. In the second stage, the mixture from stage 1 was thoroughly mixed once more, performing what is called a remill. Addition of the vulcanization system in the third stage (ready-mix stage) produced the finished mixture, with mixing at 90 to 120° C. for 180 to 300 seconds. All the mixtures were used to produce test specimens by vulcanization under pressure at 160° C. after t95 (measured on a moving die rheometer to ASTM D 5289-12/ISO 6502).

The general process for producing rubber mixtures and vulcanizates thereof is described in "Rubber Technology Handbook", W. Hofmann, Hanser Verlag 1994.

Rubber testing was effected in accordance with the test method specified in Table 2. The results of the rubber testing are reported in Table 5.

TABLE 5

|  | Mixture 7 | Mixture 8 | Mixture 9 | Mixture 10 | Mixture 20 Inv. | Mixture 21 Inv. | Mixture 22 Inv. |
|---|---|---|---|---|---|---|---|
| Rebound resilience at 23° C./% | 26.1 | 26.2 | 27.1 | 21.3 | 27.9 | 27.9 | 28.1 |
| Rebound resilience at 70° C./% | 39.8 | 39.9 | 38.8 | 39.6 | 46.8 | 46.6 | 47.2 |
| (Rebound resilience at 70° C./%) − (rebound resilience at 23° C./%) | 13.7 | 13.6 | 11.7 | 18.3 | 18.9 | 18.6 | 19.1 |

As in Example 13, the mixtures according to the invention feature improved rolling resistance compared to the comparative mixtures (rebound resilience measured at 70° C.). Again, the silane mixtures according to the invention lead to an advantageous resolution of the trade-off between rolling resistance and wet grip (difference in rebound resilience measured at 70° C. and at 23° C.). The equimolar use of the silane mixtures according to the invention demonstrates that the advantage is independent of the number of $CH_2$ units of the alkyl group in the silane of the formula I.

The invention claimed is:

1. A silane mixture comprising a silane of formula I

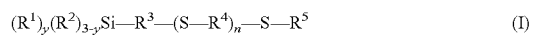

and a silane of formula II

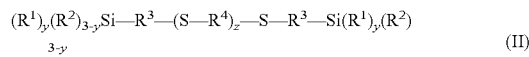

wherein $R^1$ are each independently C1-C10-alkoxy groups, phenoxy group, C4-C10-cycloalkoxy groups or alkyl polyether group —O—$(R^6$—O$)_r$—$R^7$ wherein $R^6$ are each independently a branched or unbranched, saturated or unsaturated, aliphatic, aromatic or mixed aliphatic/aromatic divalent C1-C30 hydrocarbon group, r is an integer from 1 to 30 and $R^7$ is an unsubstituted or substituted, branched or unbranched monovalent alkyl, alkenyl, aryl or aralkyl group, $R^2$ are each independently C6-C20-aryl groups, C1-C10-alkyl groups, C2-C20-alkenyl group, C7-C20-aralkyl group or halogen, $R^3$ are each independently a branched or unbranched, saturated or unsaturated, aliphatic, aromatic or mixed aliphatic/aromatic divalent C1-C30 hydrocarbon group, $R^4$ are each independently a branched or unbranched, saturated or unsaturated, aliphatic, aromatic or mixed aliphatic/aromatic divalent C1-C30 hydrocarbon group, $R^5$ is a —C(=O)—$R^8$ group wherein $R^8$ is hydrogen, a C1-C20-alkyl group, a C6-C20-aryl groups, a C2-C20-alkenyl group, a C7-C20-aralkyl group, and n is 1, 2 or 3, y are each independently 1, 2 or 3, z is 1, 2 or 3, and the molar ratio of silane of the formula I to silane of the formula II is from 20:80 to 90:10.

2. The silane mixture according to claim 1, wherein n is 1 and z is 1.

3. A process for preparing the silane mixture according to claim 2, comprising:

reacting a mercaptosilane of formula III

with a halogen compound of formula IV

wherein Hal is F, Cl, Br or I, in a molar ratio of the mercaptosilane of formula (III) to the halogen compound of formula (IV) of from 34:66 to 76:24 to obtain a product;

and reacting the product with a salt of a thiocarboxylic acid of formula (V)

or, reacting the product with NaSH and then an acid chloride of formula (VI)

4. The process for preparing the silane mixture according to claim 3, wherein the mercaptosilane of formula III is $(EtO)_3Si$—$(CH_2)_3$—SH, the halogen compound of formula IV is Cl—$(CH_2)_6$—Cl, and the thiocarboxylic acid of formula V is NaS—C(=O)—$CH_3$, NaS—C(=O)—$C_7H_{15}$ or NaS—C(=O)—$C_{17}H_{35}$.

5. The process for preparing the silane mixture according to claim 3, wherein the mercaptosilane of formula III is
$(EtO)_3Si-(CH_2)_3-SH$
the halogen compound of formula IV is
$Cl-(CH_2)_6-Cl$,
and the acid chloride of formula VI is
$Cl-C(=O)-CH_3$, $Cl-C(=O)-C_7H_{15}$ or $Cl-C(=O)-C_{17}H_{35}$.

6. The silane mixture according to claim 1, wherein the silane of formula I is $(EtO)_3Si-(CH_2)_3-(S-(CH_2)_6)_n-S-C(=O)-R^8$ and the silane of formula II is $(EtO)_3Si-(CH_2)_3-S-(CH_2)_6-S-(CH_2)_3-Si(OEt)_3$, where n is 1.

7. The silane mixture according to claim 1, wherein the silane of formula I is $(EtO)_3Si-(CH_2)_3-S-(CH_2)_6-S-C(=O)-CH_3$, $(EtO)_3Si-(CH_2)_3-S-(CH_2)_6-S-C(=O)-C_7H_{15}$ or $(EtO)_3Si-(CH_2)_3-S-(CH_2)_6-S-C(=O)-C_{17}H_{35}$ and the silane of formula II is $(EtO)_3Si-(CH_2)_3-S-(CH_2)_6-S-(CH_2)_3-Si(OEt)_3$.

8. The silane mixture according to claim 1, wherein the molar ratio of the silane of formula I to the silane of formula II is from 30:70 to 75:25.

9. A process for preparing the silane mixture according to claim 1, comprising:
mixing the silane of formula I
$$(R^1)_y(R^2)_{3-y}Si-R^3-(S-R^4)_n-S-R^5 \quad (I)$$
with the silane of formula II
$$(R^1)_y(R^2)_{3-y}Si-R^3-(S-R^4)_z-S-R^3-Si(R^1)_y(R^2)_{3-y} \quad (II)$$
in a molar ratio of 20:80-90:10.

10. The process for preparing the silane mixture according to claim 9, wherein n is 1 and z is 1.

11. The process for preparing the silane mixture according to claim 10, wherein the silane of formula I is
$(EtO)_3Si-(CH_2)_3-S-(CH_2)_6-S-C(=O)-CH_3$,
$(EtO)_3Si-(CH_2)_3-S-(CH_2)_6-S-C(=O)-C_7H_{15}$
or $(EtO)_3Si-(CH_2)_3-S-(CH_2)_6-S-C(=O)-C_{17}H_{35}$ and the silane of formula II is
$(EtO)_3Si-(CH_2)_3-S-(CH_2)_6-S-(CH_2)_3-Si(OEt)_3$.

12. The process for preparing the silane mixture according to claim 9, wherein the molar ratio of the silane of formula I to the silane of formula II is from 30:70 to 75:25.

* * * * *